(12) United States Patent
Smith et al.

(10) Patent No.: US 6,610,295 B1
(45) Date of Patent: Aug. 26, 2003

(54) PROCESSES FOR THE PRODUCTION OF HCMV GLYCOPROTEINS, ANTIBODIES THERETO AND HCMV VACCINES, AND RECOMBINANT VECTORS THEREFOR

(75) Inventors: Geoffrey Lilley Smith, Cambridge (GB); Martin Patrick Cranage, Cambridge (GB); Barclay George Barrell, Cambridge (GB)

(73) Assignee: Cogent Limited, London (GB)

(*) Notice: Subject to any disclaimer, the term of this patent is extended or adjusted under 35 U.S.C. 154(b) by 0 days.

(21) Appl. No.: 08/451,197

(22) Filed: May 26, 1995

Related U.S. Application Data

(63) Continuation of application No. 08/278,048, filed on Jul. 20, 1994, now Pat. No. 6,162,260, which is a continuation of application No. 07/899,589, filed on Jun. 18, 1992, now abandoned, which is a continuation of application No. 07/649,347, filed on Feb. 1, 1991, now abandoned, which is a continuation of application No. 07/116,566, filed on Nov. 2, 1987, now abandoned.

(30) Foreign Application Priority Data

| Mar. 7, 1986 | (GB) | 8605646 |
| Sep. 1, 1986 | (GB) | 8621081 |
| Dec. 16, 1986 | (GB) | 8629988 |
| Mar. 9, 1987 | (WO) | PCT/GB87/00164 |

(51) Int. Cl.$^7$ .................. A61K 39/395; A61K 39/42; C07K 16/00

(52) U.S. Cl. .................. 424/161.1; 424/130.1; 424/149.1; 424/159.1; 530/387.1; 530/389.1; 530/389.4; 435/69.3; 435/69.6

(58) Field of Search .................. 424/149.1, 130.1, 424/159.1, 161.1; 435/69.6, 69.3; 530/387.1, 389.1, 389.4

(56) References Cited

U.S. PATENT DOCUMENTS

| 4,670,382 A | * | 6/1987 | Buckley et al. | |
| 4,689,225 A | | 8/1987 | Pereira | |
| 4,722,848 A | | 2/1988 | Paoletti et al. | |
| 4,743,562 A | * | 5/1988 | Rasmussen et al. | 436/518 |
| 4,762,780 A | | 8/1988 | Spector et al. | |

FOREIGN PATENT DOCUMENTS

| DE | 3619720 | 12/1987 |
| EP | 0110385 | 11/1984 |
| EP | 0252302 | 1/1988 |

OTHER PUBLICATIONS

Dictionary of Science an Technology, Academic Press, 2000. http://www.harcourt.com/dictionary/def/6/6/3/8/6638700.html.*
Furukawa et al. (Proceedings of the Society for Experimental Biology and Medicine, 1984 (Feb.) vol. 175 pp. 243–250).*
Rasmussen et al. PNAS(USA) 81: 876–880, Feb. 1984a.*
Pereira et al. Virology 183: 73–86, 1984.*
Britt et al. Virology 135:369–378, 1984.*
Borysiewicz et al., "Human Cytomegalovirus–Specific Cytotoxic T Cells" *J. Exp. Med.* (1988) 168:919–931.
Britt, "Neutralizing Antibodies Detect a Disulfide–Linked Glycoprotein Complex Within the Envelope of Human Cytomegalovirus" *Virology* 135:369–378.
Cranage et al., "Identification and Expression of a Human Cytomegalovirus Glycoprotein wth Homology to the Epstein–Barr Virus BXLF2 Product, Varicella–Zoster Virus gpIII, and Herpes Simplex Virus Type I Glycoprotein H" *J. of Virology* (1988) 62:1416–1422.
Cranage et al., *Chemical Abstracts* (1986) 106:No. 62013x.
Cranage et al., "Identification of the Human Cytomegalovirus Glycoprotein in B Gene and Induction of Neutralizing Antibodies Via its Expression in recombinatnt Vaccinia Virus" *EMBO Journal* (1986) 5:3057–3063.
Farrar et al., *Vaccine* (1986) 4:217–224.
Mach et al., "Mapping of the Major Glycoprotein Gene of Human Cytomegalovirus" *J. Gen. Virol.* (1986) 67:1461–1467.
Martiney et al. *J. Virology* (1986) 60:531–38.
Mocarski et al. "Precise localization of genes on large animal virus genomes: Use of λgt11 and monoclonal antibodies to map the gene for a cytomegalovirus protein family" *PNAS USA* (1985) 82:1266–1270.
Pande et al. "Cloning and physical mapping of a gene fragment coding for a 64–kilodalton major late antigen of human cytomegalovirus" *Microbiology* (1984) 81:4965–4969.
Pereira et al. "Monoclonal Antibodies to Human Cytomegalovirus: Three Surface Membrane Proteins With Unique Immunological and Electrophoretic Properties Specify Cross–Reactive Determinants" *Infection and Immunity* (1982) 36:924–932.
Pereira et al. "Cytomegalovirus–infected Cell Polypeptides Immune–Precipitated by Sera from Children with Congenital and Perinatal Infections" *Infection and Immunity* (1983) 39:100–108.
Pereira et al. "Polymorphism of Human Cytomegalovirus Glycoproteins Characterized by Monoclonal Antibodies" *Virology* (1984) 139:73–86.
Rasmussen et al. "Human Polypeptides Detected by a Complement–Dependent Neutralizing Murine Monoclonal Antibody to Human Cytomegalovirus" *J. Virology* (1985) 55:274–280.
Rasmussen et al. "Human Cytomegalovirus Polypeptides Stimulate Neutralizing Antibody In Vivo" *Virology* (1985) 145:186–190.
Suggs et al. "Use of synthetic oligonucleotides as hybridization probes" *PNAS* (1981) 78:6613–6617.
European Search Report, Application No. EP 87 30 2001.

* cited by examiner

Primary Examiner—Mary K. Zeman
(74) Attorney, Agent, or Firm—McDonnell Boehnen Hulbert & Berghoff

(57) ABSTRACT

HCMV glycoproteins B and H have been identified. The gB protein is encoded by DNA in the HindIII F fragment of the HCMV genome lying between 1378 and 4095 bases from the F/D boundary. The gH protein is encoded by DNA in the HindIII L fragment lying between 228 and 2456 bases from the L/D boundary. The genes have been incorporated in recombinant vaccinia vectors and expressed in host animals to raise HCMV-neutralizing antibody, thereby indicating vaccine potential. The glycoproteins can also be used in a variety of different ways, as vaccines or in the production, purification or detection of HCMV antibody.

7 Claims, 12 Drawing Sheets

Fig.2(a)

```
EBV  MTRRR------------------------------------VLSVVVLLAALACRLGAQTPEQ--------------------PAPPATTVOPTATRQQ--
CMV  MESR--------------------------------IWCLVVCVNLCIVCLGAAVSSSSTSHATSSTHNGSHTSRTTSAQTRSVYSQHVTSSEAVSH
HSV  MRQGAARGCRMFVVWALLGLTLGVLASAAPSSPGTPGVAAATQAANGGPATPAPPAPGPAPTGDTKPKK

EBV  --------------------------------------------------TSFPFRVCELSSHGDLFRFSSDIQCPSF-GTRE
CMV  --------------RANETIYNTTLKYGDVVGVNTTKYPYRVCSMAQGTDLIRFERNIICTSMKPINE
HSV  NKKPKNPPPPRPAGDNATVAAGHATLRFHLRDIKAENTDANFYVCPPPTGATVVQFEQPRCPTR-PEGQ

EBV  NHTEGLLMVFKDNIIPYSFKVRSYTKIVTNILIYNGWYADSVTNRHEEKFSVDSYET-DQMDTIYQCYNA
CMV  DLDEGIMVVYKRNIVAHTFKVRVYQKVLTERRSYAYIYTTYLLGSNTEYVAPPMWEI-HHINKFAQCYSS
HSV  NYTEGIAVVFKENIAPYKFKATMYYKDVTVSQVWFGHRYSQFMGIFEDRAPVPFEEVIDKINAKGVCRST

EBV  VKHTKDGLTRVYVDRDGVNITVNLKPTGGLANGVRRYASQTELYDAPGWLIWTYRTRTTVNCLITQMMAK
CMV  YSRVIGGTVFVAYHRDSYENKTMQLIPQDYSNTHSTRYVTVKDQWHSRGSTWLYRETCNLNCMLTITTAR
HSV  AKYVRNNLETTAFHRDDHETDMELK-PANAATRTSRGWHTTDLKYNPSRVEAFHRYGTTVNCIVEEVDAR
```

Fig.2(b)

```
EBV  SNSPFDFFVTTGQTVEMSPFFYDGK-NKETFHER--ADSFHVRTNYKIVDYDNRGTNPQGERR--AFLDK
CMV  SKYPYHFFATSTGDVVYISPFFYNGT-NRNASYFGENADKEFIFPNYTIVSDFGRPNAAPETHRLVAFLER
HSV  SVPYPDEFVLATGDFVYMSPFFYGYREGSHTEHTSYAADRFKQVDGFYARDLTTKARATAPTTRNLLTTPK

EBV  GTYTLSWKLE-NRTAYCPLOHWQTEDSTIATETGKSIHFVTDEGTSSFVTNTTVGIELPDAF-KCIEEQV
CMV  ADSVISWDIQDEKNVTCQLTFWEASERTIRSEAEDSYHFSSAKMTATFLSKKQEVNMSDSAL-DCVRDEA
HSV  FTVAWDWVPK--RPSVCTMTKWQEVDEMLRSEYGGSFRFSSDAISTTFTTNLTEYPLSRVDLGDCIGKDA

EBV  NKTMHEKYEAVQDRYTKGQEAITYFITSGGLLLAWLPLTPRSLATVKNLTELTTPTSSPPSSPSPPAPSA
CMV  INKLQQIFNTSYNGTYEKYGNVSVFETSGGLVVFWQGIKQKSLVELERLANRSSLNITHRTRRST-----
HSV  RDAMDRIFARRYNATHIKVGQPQYYLANGGFLIAYQPLLSNTLAELYVREHLREQSRKPPNPTPPPPGAS

EBV  NKTMHEKYEAVQDRYTKGQEAITYFITSGGLLLAWLPLTPRSLATVKNLTELTTPTSSPPSSPSPPAPSA
CMV  INKLQQIFNTSYNGTYEKYGNVSVFETSGGLVVFWQGIKQKSLVELERLANRSSLNITHRTRRST-----
HSV  RDAMDRIFARRYNATHIKVGQPQYYLANGGFLIAYQPLLSNTLAELYVREHLREQSRKPPNPTPPPPGAS
```

Fig. 2(c)

```
EBV  ARGSTPAAVLRRRRDAGNATTPVPPTAPGKSLGTLNNPATVQIQFAYDSLRRQINRMLGDLARAWCLEQ
CMV  --------------SDNNTTHLSSMESVH------NLVYAQLQFTYDTLRGYINRALAQIAEAWCVDQ
HSV  -----------------ANASVERIKTTSSIEF---------ARLQFTYNHIQRHVNDHLGRVAIAWCELQ

EBV  KRQNMVLRELTKINPTTVMSSIYGKAVAAKRLGDVISVSQCVPVNQATVTLRKSMRVPGSETMCYSRPLV
CMV  RRTLEVFKELSKINPSAILSAIYNKPIAARFMGDVLGLASCVTINQTSVKVLRDMNVKESPGRCYSRPVV
HSV  NHELTLWNEARKLNPNAIASATVGRRVSARHLGDVMAVSTCVPVAADNVIVQNSMRISSRPGACYSRPLV

EBV  SFSFINDTKTYEGQLGTDNEIFLTKKMTEVCQATSQYYFQSGNEIHVYNDYHHFKTIELDGIATLQTFIS
CMV  IFNFANSSYVQYGQLGEDNEILLGNHRTEECQLPSLKIFIAGNSAYEYVDYLFKRMIDLSSISTVDSMIA
HSV  SFRYEDQGPLVEGQLGENNELRLTRDAIEPCTVGHRRYFTFGGGYVYFEEYAYSHQLSRADITTVSTFID

EBV  LNTSLIENIDFASLELYSRDEQRASNVFDLFGIFREYNFQAQNIAGLRKDLQNAVSNGRNQFVD|GLGELH|
CMV  LDIDPLENTDFRVLELYSQKELRSSNVFDLEEIMREFNSYKQRVK   YVEDKVVDDPLPPYLK|GLDDLM|
HSV  LNITMLEDHEFVPLEVYTRHEIKDSGLLDYTEVQRRNQLHQLRFA---DIDTVIHADANAAMFA|GLGAFF|
```

*Fig.2(d)*

```
EBV  DSLGSVGQSITNLVSTVGGLFSSLVSGFISF FKNP FGGMLILVLVAGVVILVISLT RRTRQMSQQPVQML
        ::    :                     ::  ::::  ::  :: ::::::::  ::
CMV  SGLGAAGKAVGVAIGAVGGAVASVVEGVATFL KNP FGAFTIILVAIAVVIITYLIY TRQRRLCTQPLQNL
         :  ::    :   ::    ::  :  ::  ::: ::   :: :: ::  :    ::    :
HSV  EGMGDLGRAVGKVVMGIVGGVVSAVSGVSSFHSNPF GALAVGLLVLAGLAAAFFAF RYVNRLQSNPMKAL

EBV  YPGI-DELAQQH---ASGEGPGINPISKTELQ-AIMLALHEQNQEQKRAAQRAAGPSVASRALQAAARDRF
        ::
CMV  FPYLVSADGTTVTSGSTKDTSLQAPPSYEESVYNSGRKGPGPASSDASTAAPPYTNEQAYQMLLALARLD
       ::  ::                  ::               ::
HSV  YPLTTKELKNPTNPDASGEGEEGGDFDEAKLAEAREMIRYMALVSAMERTEHKAKKGTS-ALLSAKVTD

EBV  PGLRRRRYHDPETAAALLGEA-ETEF
        ::
CMV  AEQRAQQNGTDSLDGQTGTQDKGQKPNLLDRLRHRKNGYRHLKDSDEEENV
                  ___
HSV  MV MRKRRNTNYTQVPNKDGDADEDDL
            ___
```

```
     F G R P N A A P E T H R L V A F L E R A D S V I S M D I Q D E K N V T C Q L T F
1081 TTTGGAAGACCCAACGCTGGCCCAGAAACCCATAGGTTGGTGGTTTTCTTGAACGTCCGACTCGGTGATCTTTGGATATACGACAGAAGAATGTCACCTGCCAGCTCACCTTC

W E A S P R T I R S E A E D S Y H F S S A K H T A T F L S K K Q E V N M S D S A
1201 TGGGAAGCCTCGGAACCTACTATCCGTTCCGAAGCCGAAGACTCGTACCACTTTCTTCTTTGCCAAAATGACTGCAACTTTCTGTCTAAGAAACAAGAAGTGAACATGTCCGATTCCGCG

L D C V R D E A I N K L Q Q I F N T S Y N Q T Y E K Y G N V S V F E T S G G I V
1321 CTGGACTGCGTACGTACGTGATGAGCGTATAAATAAGTTACAGCAGATTTTCAAGACTTCATACAATCAAACATATCAAAAATACGGAACGTGTCCGTTCGAAACCAGCGGCGGTTGTC

V F W Q G . I K Q K S L V E L E R L A N R S S L N I T H R T R R S T S D N N T T H
1441 GTGTTCTGGCAAGGCATCAAGCAAAAATCTTTGGTGGAATTGGAACGTTGGCCAATCGATCCAGTCAGTCTGAATATCACTCATAGGACCAGAAGAGTACGAGTGACAATACAACTCAL

L S S H E S V H N L V Y A O L O F T Y D T L R G Y I N R A L A O I A E A W C V D
1561 TTGTCCAGCATGAATGGTCCACAATTCGTCTACGCCCAGCTGCAGTTCACCTATGACCGTTGGCGGGTTACATCAACCGGGCTGCCCAAATCCGAGAGCCTTGGTCTTGTGTGGAT

Q R R T L E V F K E L S K I N P S A I L S A I Y N K P I A A R F M G D V L G L A
1681 CAACGGCGCACCCTAGAGGTCTCAAGGAACTCAGCAAGATCAACCCGTCAGCCATTCTCTCGGCCATTTACAACAAACCGATTGCCGGCGTTCATGGGTGATGTCTTGGCCTGGCC

S C V T I N Q T S V K V L R D M H N V K E S P G R C Y S R P V V I F N F A N S S Y
1801 AGCTGCGTGACCATCAACCAAACCAGCGTCAAGGTGCTCAGGGATATGCACAATGTGAAGGAATCGCCAGGACGTGCTACTCAGACCCGTGTCATCTTTAATTTGCCAACAGCTGTAC

V Q Y G Q L G E D N E I L L G N R R T E E C O L P S L K I F J A G N S A Y E Y V
1921 GTGCAGTACGGTCAACTGGGGGAGGACAACGAAATCCTGTTGGGCAACCACCGCACTGAGGAATGTCAGCTTCCCAGCCTCAAGATCTTCATCGCCGGGACTCGGCCTACGAGTACGTG

D I L F K R M D L S S I S T V D S M I A L D I D P L E N T D F R V L E L Y S Q
2041 GACTACCTCTTCAAACGCATGATTGACCTCAGCAGTATCTCCACGGTCGACAGCATGATCGCCCTGGATATCGACCCGCTGGAAATACCGACTTCAGGTACTGGAACTTACTCGCAG
```

Fig.3(c)

```
            K   E   L   R   S   S   N   V   F   D   L   E   E   I   M   R   E   F   N   S   Y   K   Q   R   V   K   T   Y   E   D   K   V   V   D   P   L   P   P   Y   L
2161   AAAGAGCTGCGTTCCAGCAACGTTTTTGACCTGGAAGAGATCATGCGGGAATTCAACTCGTACAAGCAGCGGGTAAAGTACTACTGGAGGACAAGGTAGTCGACCCGCTACCGCTACCTC

K   G   L   D   D   L   H   S   G   L   G   A   A   G   K   A   V   G   V   A   I   G   A   V   G   G   A   V   A   S   V   V   E   G   V   A   T   F   L   K
2281   AAGGGTCTGGACGACCTCCATGAGCGGCCTGGGCGCCGCGGGAAAGGCCGTTGGCGTAGCCATTGGGGCCGTTGGCGGGGCCGTTGCCTCCGTTGTCGAAGGCGTTGCCACCTTCCTCAAA

N   P   F   G   A   F   T   I   I   L   V   A   I   A   V   V   I   I   T   T   L   I   Y   T   R   Q   R   R   L   C   T   Q   P   L   Q   N   L   F   P   Y
2401   AACCCCTTCGGAGCCTTCACCATCATCCTCGTCGCCATAGCCGTAGTCATTATCACTACTCTTATTTATACTCGACAGCGGCGTCTGTGCACGCAGCCGCTGCAGAACCTCTTTCCCTAT

L   V   S   A   D   G   T   T   V   T   S   G   S   T   K   D   T   S   L   Q   A   P   P   S   Y   E   E   S   V   Y   N   S   G   R   K   G   P   G   P   P
2521   CTGGTGTCCGCGGACGGGACCACCGTGACGTCGGGCAGCACCAAAGACACGTCGTTACAGGCTCCCCCTTCCTACGAGGAAAGTGTTTATAATTCTGGTCGCAAAGGACCGGGACCACCG

S   S   D   A   S   T   A   A   P   P   T   T   N   E   Q   A   Y   Q   M   L   L   A   L   A   R   L   D   A   E   Q   R   A   Q   Q   N   G   T   D   S   L
2641   TCGTCTGATGCATCCAGCGGGGCCTCCCCTTACCAACGACAGCCAGGCTTACCAGATACTCTTGGCCCTGGCCCGTCTGGACGCAGAGCAGCGGGCCGAGCGGCAGCGGTACAGATTCTTG

D   G   Q   T   G   Q   D   K   G   Q   K   P   N   L   L   D   R   L   R   R   K   R   K   N   G   Y   R   N   L   K   D   S   D   E   E   N   V
2761   GACGGACAGACTGGCCAGGACAAGGGACAGAAGCCTAACCTGCTAGACCGGCTGAGACGCAAAAGGCTACAGACACTTGAAAGACTCCGAAGAAGAACGTCGAACC

2881   AGGAGGAAAAAAAACTAGACAAAAATATTGACACAGAGACTTGTGATATCTAGGTGCTGCATGTGTATTTCTTGTGATTTGCTTCGTAAGCGTCA

3001   GCCTTCTCACGGTCCGCTATGTTTTTCAACCGTATCTGAGCGGCGTCGGGGTGCCGGGTGACCGGCGGCGTCCAGCCGGTTCAGCGTTCAGCGTTCCGCAGCCCCGGTCCCGCAGGGCTCGGGCAAGC

3121   GGCCG
```

Fig. 5(a)

```
  1 CGCAGAGCGTTCCCCGTCGAATCAGCGTCGTCCCCACGCCCGGACGGCATGGCTTACCCG
 61 CGTGTCCCCTCTTCTTCCTTCGCAGCGGCCAATGACATCGTATTAAATAGACAGAGACGC
121 GACTTTTGTAACCCGTAGCGCCACACCCGGGTGCCCCTTCCTGGGATCCTTTCTCTCCTT
                                  SmaI
181 CTCTCGGGTGTAACGCCAACCACCACCTGGATCACGCCGCTGAACCCAGCGGCGCAGCC.
           M  R  P  G  L  P  P  Y  L  T  V  F  T  V  Y  L  L  S  H
241 CGCTATGCGGCCCGGCCTCCCCCCCTACCTCACTGTCTTCACCGTCTACCTCCTCAGTCA
        L  P  S  Q  R  Y  G  A  D  A  A  S  E  A  L  D  P  H  A  F
301 CCTACCTTCGCAACGATATGGCGCGGACGCCGCATCCGAAGCGCTGGACCCTCACGCATT
        H  L  L  L  N  T  Y  G  R  P  I  R  F  L  R  E  N  T  T  Q
361 TCACCTACTACTCAACACCTACGGGAGACCCATCCGCTTCCTGCGTGAAAACACCACCCA
        C  T  Y  N  S  S  L  R  N  S  T  V  V  R  E  N  A  I  S  F
421 GTGCACCTACAACAGCAGCCTCCGTAACAGCACGGTCGTCAGGGAAAACGCCATCAGTTT
        N  F  F  Q  S  Y  N  Q  Y  Y  V  F  H  M  P  R  C  L  F  A
481 CAACTTTTTCCAAAGCTATAATCAATACTATGTATTCCATATGCCTCGATGTCTTTTTGC
        G  P  L  A  E  Q  F  L  N  Q  V  D  L  T  E  T  L  E  R  Y
541 GGGTCCTCTGGCGGAGCAGTTTCTGAACCAGGTAGATCTGACCGAAACCCTAGAAAGATA
        Q  Q  R  L  N  T  Y  A  L  V  S  K  D  L  A  S  Y  R  S  F
601 CCAACAGAGACTTAACACCTACGCATTGGTATCCAAAGACCTGGCCAGCTACCGATCTTT
        S  Q  Q  L  K  A  Q  D  S  L  G  Q  Q  P  T  T  V  P  P  P
661 TTCGCAGCAGCTGAAGGCACAAGACAGCCTGGGTCAGCAGCCCACCACCGTGCCACCGCC
        I  D  L  S  I  P  H  V  W  M  P  P  Q  T  T  P  H  D  W  K
721 CATTGATCTGTCAATACCTCACGTTTGGATGCCACCCCAAACCACTCCACACGACTGGAA
        G  S  H  T  T  S  G  L  H  R  P  H  F  N  Q  T  C  I  L  F·
781 GGGATCGCACACCACCTCGGGACTACATCGGCCACACTTTAACCAGACCTGTATCCTCTT
        D  G  H  D  L  L  F  S  T  V  T  P  C  L  H  Q  G  F  Y  L
841 TGATGGACACGATCTGCTTTTCAGCACCGTTACGCCCTGTCTGCACCAGGGCTTTTACCT
        M  D  E  L  R  Y  V  K  I  T  L  T  E  D  F  F  V  V  T  V
901 CATGGACGAACTACGTTACGTTAAAATCACACTGACCGAGGACTTCTTCGTAGTTACGGT
        S  I  D  D  D  T  P  M  L  L  I  F  G  H  L  P  R  V  L  F
961 ATCTATAGACGACGACACACCCATGCTGCTTATCTTCGGTCATCTTCCACGCGTACTCTT
```

Fig.5(b)

```
              K   A   P   Y   Q   R   D   N   F   I   L   R   Q   T   E   K   H   E   L   L
1021  CAAAGCGCCCTATCAACGCGACAACTTTATACTACGACAAACTGAAAAACACGAGCTCCT

V   L   V   K   K   A   Q   L   N   R   H   S   Y   L   K   D   S   D   F   L
1081  GGTACTAGTTAAGAAAGCTCAACTAAACCGTCACTCCTATCTCAAAGACTCGGACTTTCT

D   A   A   L   D   F   N   Y   L   D   L   S   A   L   L   R   N   S   F   H
1141  CGACGCCGCACTCGACTTCAACTACCTGGACCTCAGCGCACTGTTACGTAACAGCTTTCA

R   Y   A   V   D   V   L   K   S   G   R   C   Q   M   L   D   R   R   T   V
1201  CCGTTACGCTGTAGACGTACTCAAAAGCGGTCGATGTCAAATGTTGGACCGCCGCACGGT

E   M   A   F   A   Y   A   L   A   L   F   A   A   A   R   Q   E   E   A   G
1261  AGAAATGGCCTTCGCCTACGCATTAGCACTGTTCGCGGCAGCCCGACAAGAAGAGGCCGG

T   E   I   S   I   P   R   A   L   D   R   Q   A   A   L   L   Q   I   Q   E
1321  CACCGAAATCTCCATCCCACGAGCCCTAGACCGCCAGGCCGCACTCTTACAAATACAAGA

F   M   I   T   C   L   S   Q   T   P   P   R   T   T   L   L   Y   P   T
1381  ATTTATGATCACCTGCCTCTCACAAACACCACCACGCACCACATTGCTGCTATATCCCAC

A   V   D   L   A   K   R   A   L   W   T   P   D   Q   I   T   D   I   T   S
1441  AGCCGTGGACCTGGCCAAACGAGCCCTCTGGACGCCGGACCAGATCACCGACATCACCAG

L   V   R   L   V   Y   I   L   S   K   Q   N   Q   Q   H   L   I   P   Q   W
1501  CCTCGTACGCCTGGTCTACATACTTTCTAAACAGAATCAGCAACATCTCATTCCCCAGTG

A   L   R   Q   I   A   D   F   A   L   Q   L   H   K   T   H   L   A   S   F
1561  GGCACTACGACAGATCGCCGACTTTGCCCTACAATTACACAAAACGCACCTGGCCTCTTT

L   S   A   F   A   R   Q   E   L   Y   L   M   G   S   L   V   H   S   M   L
1621  TCTTTCAGCCTTCGCGCGCCAAGAACTCTACCTCATGGGCAGCCTCGTCCACTCCATGTT

V   H   T   T   E   R   R   E   I   F   I   V   E   T   G   L   C   S   L   A
1681  GGTACATACGACGGAGAGACGCGAAATCTTCATCGTAGAAACGGGCCTCTGTTCATTGGC

E   L   S   H   F   T   Q   L   L   A   H   P   H   H   E   Y   L   S   D   L
1741  CGAGCTATCACACTTTACGCAGTTGCTAGCTCATCCGCACCACGAATACCTCAGCGACCT

Y   T   P   C   S   S   S   G   R   R   D   H   S   L   E   R   L   T   R   L
1801  GTACACACCCTGTTCCAGTAGCGGGCGACGCGATCACTCGCTCGAACGCCTCACGCGTCT

F   P   D   A   T   V   P   A   T   V   P   A   A   L   S   I   L   S   T   M
1861  CTTCCCCGATGCCACCGTTCCTGCTACCGTTCCCGCCGCCCTCTCCATCCTATCTACCAT

Q   P   S   T   L   E   T   F   P   D   L   F   C   L   P   L   G   E   S   F
1921  GCAACCAAGCACGCTGGAAACCTTCCCCGACCTGTTTTGTCTGCCGCTCGGCGAATCCTT
```

Fig.5(c)

```
       S   A   L   T   V   S   E   H   V   S   Y   V   V   T   N   Q   Y   L   I   K
1981 CTCCGCGCTAACCGTCTCCGAACACGTCAGTTATGTCGTAACAAACCAGTACCTGATCAA

G   I   S   Y   P   V   S   T   T   V   V   G   Q   S   L   I   I   T   Q   T
2041 AGGTATCTCCTACCCTGTCTCCACCACCGTCGTAGGCCAGAGCCTCATCATCACCCAAAC

D   S   Q   T   K   C   E   L   T   R   N   M   H   T   T   H   S   I   T   A
2101 GGACAGTCAAACTAAATGCGAACTAACGCGCAACATGCACACCACACACAGCATCACAGC

A   L   N   I   S   L   E   N   C   A   F   C   Q   S   A   L   L   E   Y   D
2161 GGCGCTCAACATTTCACTAGAAAACTGCGCCTTTTGCCAAAGCGCCCTGCTAGAATACGA

D   T   Q   G   V   I   N   I   M   Y   M   H   D   S   D   D   V   L   F   A
2221 CGACACGCAAGGCGTCATCAACATCATGTACATGCACGACTCGGACGACGTCCTTTTCGC

L   D   P   Y   N   E   V   V   V   S   S   P   R   T   H   Y   L   M   L   L
2281 CCTGGATCCCTACAACGAAGTGGTGGTCTCATCTCCGCGAACTCACTACCTCATGCTTTT

K   N   G   T   V   L   E   V   T   D   V   V   V   D   A   T   D   S   R   L
2341 GAAAAACGGTACGGTCCTAGAAGTAACTGACGTCGTCGTGGACGCCACCGACAGTCGTCT

L   M   M   S   V   Y   A   L   S   A   I   I   G   I   Y   L   L   Y   R   M
2401 CCTCATGATGTCCGTCTACGCGCTATCGGCCATCATCGGCATCTATCTGCTCTACCGCAT

L   K   T   C
2461 GCTCAAGACATGCTGACTGTAGAACCTGACAGTTTATGAGAAAAGGGACAGAAAAGTTAA

2521 AGACATTCACACAAAATCTTCTAAAACGGTACGGGCCCCAATACTTAGGGGCACTCTTGC

2581 TCGTTGTAATAAAGTACACGCCACACGGTGTGATGGTACTATATGCGTGAGGTCTGTGCG

2641 TCTTTATTTACGAGGTACTGTTATGGGTCTGGTTACATATCGGGCCCTGGATACAAGCTT
                                                              HindIII
```

US 6,610,295 B1

PROCESSES FOR THE PRODUCTION OF HCMV GLYCOPROTEINS, ANTIBODIES THERETO AND HCMV VACCINES, AND RECOMBINANT VECTORS THEREFOR

This application is a continuation of application Ser. No. 08/278,048 filed Jul. 20, 1994, now U.S. Pat. No. 6,162,620 which is a continuation of application Ser. No. 07/899,589 filed Jun. 18, 1992, abandoned, which is a continuation of application Ser. No. 07/649,347 filed Feb. 1, 1991, abandoned, which is a continuation of application Ser. No. 07/116,566 filed Nov. 2, 1987 abandoned.

FIELD OF INVENTION

This invention relates to human cytomegalovirus (HCMV), and is concerned with the production of glycoproteins of the virus, their vaccine potential, and the production of HCMV specific antibodies.

BACKGROUND TO THE INVENTION

HCMV is a human pathogen of considerable importance and there is a demand for an effective vaccine against it. Hitherto experimental vaccines have been based on attenuated, non-pathogenic forms of the virus, but these can have undesirable side effects. The invention provides an alternative approach to the production of a vaccine against HCMV, using recombinant DNA techniques.

Like other herpes viruses HCMV specifies multiple glycoproteins (1,2). Characterisation of these have involved studies of CMV-infected cells and purified virions using polyclonal sera and monoclonal antibodies (2–10). One glycoprotein has been partially purified and shown to elicit a neutralising response in guinea pigs. However, the total number of HCMV-specified glycoproteins remains uncertain and the vaccine potential of individual glycoprotein is unknown. Purification of individual glycoproteins from HCMV-infected cells is a daunting prospect because the virus grows slowly and fails to shut down host cell protein synthesis during infection.

SUMMARY OF THE INVENTION

The present invention is based on the identification and expression of HCMV DNA encoding two glycoproteins, referred to herein as gB and gH. The gB protein is encoded by DNA in the HindIII F fragment of the HCMV genome lying between 1378 and 4095 bases from the F/D boundary. The gH protein is encoded by DNA in the HindIII L fragment lying between 228 and 2456 bases from the L/D boundary.

According to one aspect of the present invention there is provided a process which comprises expressing from a recombinant DNA vector in a suitable host organism a polypeptide incorporating one or more antigenic determinants capable of rising HCMV-neutralising antibodies in humans, said determinant or determinants corresponding to a portion of the protein encoded by DNA in the HindIII F fragment of the HCMV genome lying between 1378 and 4095 bases from the F/D boundary and/or a portion of the protein encoded by DNA in the HindIII L fragment of the HCMV genome lying between 228 and 2456 bases from the L/D boundary.

A second aspect of the present invention provides a recombinant virus vector containing DNA encoding such a polypeptide, said vector being capable of infecting a human subject and expressing the polypeptide in immunogenic form.

A third aspect of the present invention provides a process which comprises synthesising such a polypeptide.

A fourth aspect of the present invention provides a method of preparing HCMV monospecific antiserum comprising immunising a host animal with such polypeptide or with a recombinant virus vector as described above, and extracting from the host animal antiserum specific to said polypeptide. HCMV-specific monoclonal antibody may be prepared from cells from such immunised animals.

A fifth aspect of the present invention provides a method of purifying HCMV-specific antibodies, which comprises contacting the antibodies with HCMV polypeptide hereof, and separating bound antibody from the polypeptide.

A sixth aspect of the present invention provides a method of detecting HCMV-specific antibody in a clinical sample, which comprises contacting the sample with HCMV polypeptide hereof, and detecting antibody that binds to the polypeptide.

A seventh aspect of the present invention provides a kit for carrying out such a detection method, the kit comprising said polypeptide in a form suitable for contacting with the clinical sample, and means for detecting HCMV-specific antibody that binds to said polypeptide.

By identifying surface glycoprotein(s) of HCMV that lead to an immune response and incorporating the corresponding sequence of genetic material in a mammalian vector, an immunologically active protein may be produced which can form the basis of a vaccine against HCMV.

For the recombinant virus vaccine the identified HCMV genome fragment may be isolated and introduced into a suitable mammalian virus vector by conventional genetic engineering techniques, and transfecting the plasmid into a mammalian host.

Suitable vectors include mammalian cells and viruses such as poxviruses, with vaccinia virus being particularly preferred, and bovine papilloma virus.

Expression of the foreign DNA can be obtained by infecting cells or animals with recombinant virus vector. For example, a recombinant virus, e.g. vaccinia virus, may be used as a live vaccine. Further, cells infected with the recombinant vector may be used to prepare the product of the foreign DNA for use as a vaccine.

In one preferred technique, a glycoprotein-encoding fragment of the HCMV genome is introduced into plasmid pGS62 and then transferred into vaccinia virus by transfecting the plasmid into mammalian cells infected with vaccinia virus.

It will be apparent that the HCMV DNA may be modified in various ways without significantly affecting the functioning of the protein produced thereby. For example, a transmembrane form of protein may be converted to a secreted form by removing the DNA coding for the C-terminal containing the membrane anchor sequence. Such modifications are to be considered within the scope of the present invention.

BRIEF DESCRIPTION OF THE DRAWINGS

FIGS. 2A–2D are a comparison of the predicted translation products of the HCMV gB gene identified in FIG. 1 (designated CMV) with those of glycoprotein B of herpes simplex virus type 1 (designated HSV) and a possible Epstein Barr virus glycoprotein (designated EBV). The potential glycosylation sites are underlined, and the hydrophobic putative signal and anchor regions are shown boxed.

FIGS. 3A–3C are the DNA sequence of the XmaIII restriction enzyme fragment of the HindIII F fragment of the HCMV genome, including the gene coding for HCMV gB, showing the deduced amino acid sequence of HCMV gB. For clarity this is shown in the opposite orientation to which it occurs in the prototype orientation of the HCMV genome.

FIGS. 5A–5C show the DNA sequence of the SmaI-HindIII L fragment spanning the coding sequence for HCMV gH. As with FIG. 3, this is shown in the opposite orientation to which it occurs in the prototype orientation of the HCMV genome. The deduced amino acid sequence of HCMVgH is shown above the DNA sequence in the one letter amino acid code. The restriction enzyme recognition sequences for SmaI (CCCGGG) and HindIII (AAGCTT) used in the cloning are underlined, and the potential glycosylation sites are overlined. The HindIII site delineates the boundary between the HindIII fragments L and D in the genome. The hydrophobic putative signal and anchor regions are shown boxed.

The invention will be further illustrated by the following Examples.

EXAMPLES

Identification of Putative Glycoprotein Genes

In order to look for possible glycoprotein genes within the HCMV genome individual cloned restriction fragments of the genome of HCMV strain AD169 were sequenced using the M13/dideoxynucleotide chain termination method described in reference (11) using the strategy and methods described by Bankier and Barrell in reference (12). The resulting compiled sequences were then analysed for possible protein coding sequences and RNA polymerase II transcription signals. The predicted translation products of likely protein coding sequences were then examined for the presence of glycoprotein characteristics, namely an N-terminal hydrophobic signal peptide, a hydrophobic transmembrane sequence close to the C-terminus, and potential N-glycosylation sites in the external domain.

Figure 1:
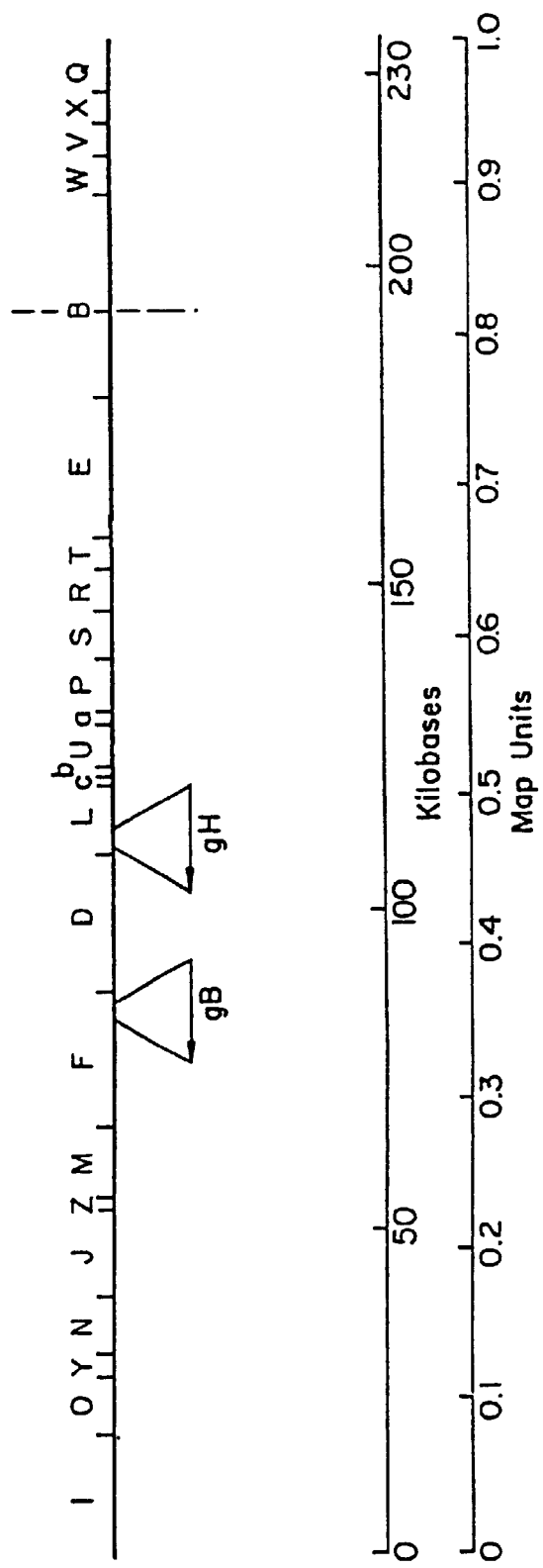
FIG. 1 is a map of the HCMV genome strain AD169 in the prototype orientation showing cleavage sites for the restriction enzyme HindIII, illustrating the position and orientation of the genes encoding HCMV gB and HCMV gH.

Using these criteria two putative glycoprotein genes were identified lying between bases 16255 and 18972 of the HindIII F fragment and between base 228 and 2456 of the HindIII L fragment, respectively, of HCMV DNA. A HindIII fragment map of the HCMV genome is shown in FIG. 1. In FIG. 1 the vertical dashed line delineates the long and short unique regions of the viral DNA respectively. The capital letters refer to the fragments produced by HindIII cleavage—see reference (13). The positions and orientation of the glycoprotein genes B and H are shown in the HindIII restriction fragments F and L, respectively. The coding region of the glycoprotein B lies between bases 1378 and 4095 from the HindIII F/D boundary on the complementary strand of the DNA sequence; while that of the glycoprotein H lies between bases 228 and 2456 from the HindIII L/D boundary on the complementary strand of the DNA sequence.

The HCMV Glycoprotein B

The primary translation product of the glycoprotein B gene in the indicated open reading frame is a 906 amino acid polypeptide containing 16 potential N-linked glycosylation sites. There is a hydrophobic sequence close to the N-terminus which may function as a signal sequence, and stretches of hydrophobic amino acids at its C-terminus which may function as anchor sequences. The predicted translation product of this gene was compared with glycoprotein genes of other human herpes viruses. The search revealed homology with glycoprotein B (gB) of herpes simplex virus (HSV) and Epstein Barr virus (EBV) (reference 14); Varicella zoster (VZV) also possesses a glycoprotein gene with homology. For this reason the protein encoded by this reading frame is subsequently referred to as HCMV gB.

A comparison of the predicted translation product HCMV gB with those of HSV1 and EBV is shown in FIG. 2. The predicted HCMV glycoprotein sequence is aligned with those found in EBV and HSV1. The sequences are displayed in the one letter amino acid code and have been aligned and padded with dashes to produce as far as possible an optimum alignment of homologous amino acids. In regions where there is little homology, e.g. at the ends, the alignment is arbitrary. Regions of hydrophobic amino acids at the N-terminus and near the C-terminus which are characteristic of glycoproteins are boxed and potential N-linked glycosylation sequences (N*T or N*S, where * is any amino acid) are underlined.

FIG. 2 shows good alignment of the gB proteins of HSV-1, EBV and HCMV and demonstrates that the proteins are homologous along a large proportion of their length with the N- and C-termini showing least conservation. It can be seen that at 121 positions there is an identically matched amino acid in all three proteins. Taken as a proportion of EBV gB this means that over 14% of the protein is perfectly conserved. Furthermore, all 10 cysteine residues present between the putative signal and anchor sequences are perfectly aligned, suggesting that the extracellular portion of the proteins may possess a similar overall structure. The extent of the homology between the three viral proteins provides convincing evidence that the putative HCMV glycoprotein is that of glycoprotein B. Further evidence of its glycoprotein character is provided by its characteristic hydrophobic regions and potential N-glycosylation sites which are shown in FIG. 2.

To investigate the nature of the HCMV gB and to raise antisera against this protein the gene was excised from the HindIII F fragment of the HCMV genome and expressed in recombinant vaccinia virus. This vector system is suitable for the expression of eukaryotic virus glycoprotein genes because the proteins are correctly processed and inserted into the infected cell membrane. In addition, the infectious recombinant virus may be used to raise monospecific antisera against the foreign protein in vaccinated animals.

Figure 3A:
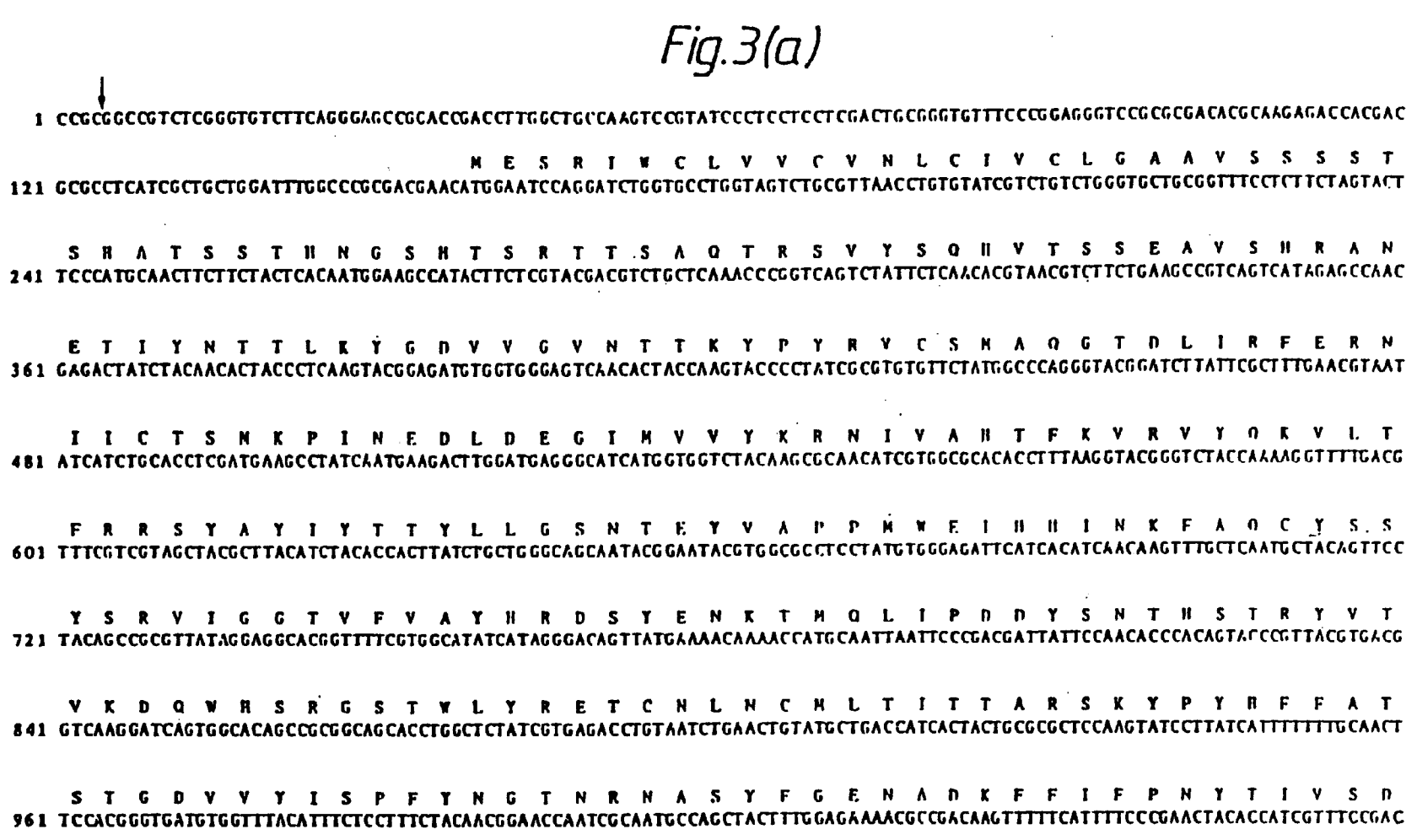

The coding sequence shown in FIG. 3 was introduced into vaccinia virus as described below. The sequences shown in FIGS. 2 and 3 are displayed in the commonly used form 5' to 3' in the coding sense sequences. This is in the opposite orientation to the prototype orientation of the HCMV genome shown in FIG. 1. The amino acid sequence of the HCMV gB is shown above the DNA sequence using the one letter amino acid code.

Construction of Recombinant Vaccinia Virus Expressing HCMV gB

1. Strategy

Expression of foreign genes in vaccinia virus is dependent upon the use of vaccinia promoters (for review see reference 15). This is due to the unique nature of vaccinia promoters and the presence of the vaccinia RNA polymerase which does not recognise promoters that are transcribed by RNA polymerase II. Several plasmids that are designed to facilitate expression of foreign genes in vaccinia virus have been constructed (see references 16 to 18). They contain a vaccinia promoter and downstream restriction endonuclease sites translocated within the body of the thymidine kinase (TK) gene. A foreign protein coding sequence may then be positioned downstream of the vaccinia promoter and inserted into the vaccinia genome by homologous recombination in vivo (see reference 17). Authentic foreign proteins are made provided that the junction between vaccinia promoter and foreign protein coding sequences is engineered to use the translation initiation codon of the foreign gene.

Inspection of the nucleotide sequence of the HCMV gB gene and adjacent DNA showed that presence of restriction endonuclease XmaIII sites 148 nucleotides upstream and 251 nucleotides downstream of the gB coding sequences. Additionally, there were no potential translation initiation codons between the upstream XmaIII site and the ATG codon initiating the gB open reading frame. The strategy was, therefore, to excise the gB gene from the HCMV HindIII F fragment as a 3.1 kb fragment and clone this fragment into the SmaI site of plasmid insertion vector pGS62 (a derivative of pGS20—see reference 17—in which an EcoRI site upstream of the vaccinia promoter has been deleted). In this way the gB gene would be under control of a vaccinia promoter that is expressed throughout the vaccinia virus replicative cycle. Direct isolation of the desired fragment was difficult due to the large size of the HCMV HindIII F fragment and presence of other XmaIII sites.

2. Experimental

Figure 4:
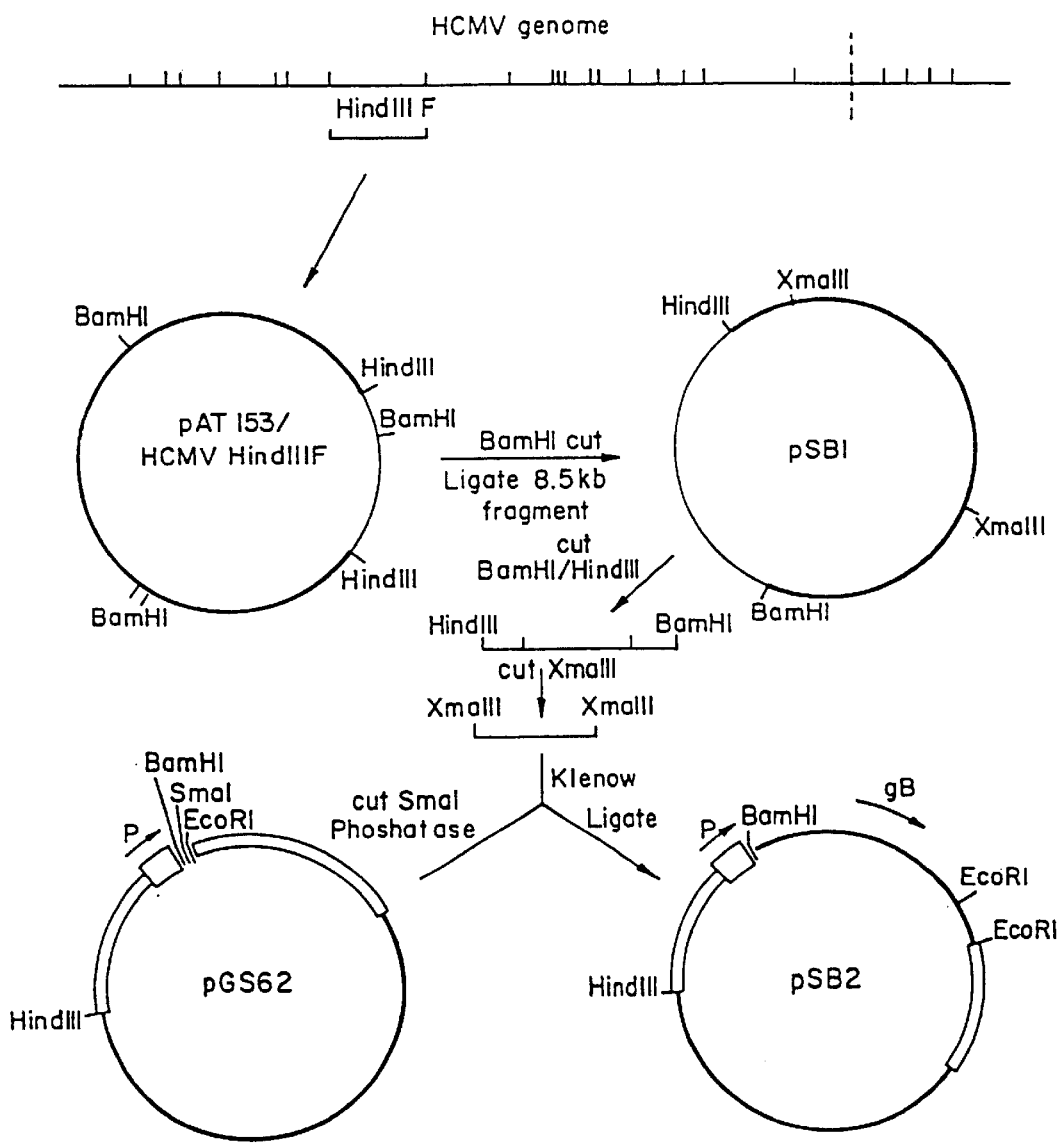
FIG. 4 illustrates introduction of the sequence of FIG. 3 into plasmid pGS62 from which it can be transferred into vaccinia virus. Thick line indicates HCMV DNA; and thin line indicates plasmid DNA. Open box indicates vaccinia DNA taken from the vaccina HindIII J fragment and including the TK gene coding sequences into which a vaccinia promoter P has been translocated.

Considering the matter in more detail, the coding sequence of FIG. 3 was introduced into vaccinia virus by the following series of manipulations which are illustrated in FIG. 4.

a) The HindIII F fragment cloned into a truncated pAT153 (see reference 19) was digested with BamHI and after separation of the products by electrophoresis the 8.5 kb fragment was isolated and self ligated to generate plasmid pSB1 (also known pSCB1). pSB1 contains a 5 kb HindIII/BamHI fragment of the HCMV HindIII F cloned into the 3.5 kb HindIII/BamHI fragment of pAT153.

b) pSB1 was digested with BamHI and HindIII and the 5.0 kb HCMV fragment was isolated and digested with XmaIII. The resulting 3.1 kb XmaIII fragment was isolated, the 5' overhangs repaired with *E. coli* DNA polymerase I Klenow fragment, and the repaired fragment ligated into the SmaI site of plasmid pGS62. pGS62 contains the vaccinia virus thymidine kinase (TK) gene interrupted by a vaccinia promoter element. Insertion of a foreign gene at the SmaI site results in a plasmid in which the foreign HCMV gB gene is under the control of the vaccinia promoter (P) and is flanked by thymidine kinase coding sequences.

The orientation of the gB gene within the resultant plasmid pSB2 was determined using a unique EcoRI site present 911 nucleotides from the 3' XmaIII site as a convenient marker.

Recombinant plasmids were identified by increase in size, and the orientation of the 3.1 kb insert was determined by EcoRI digestion. A plasmid containing the XmaIII fragment in the correct orientation with respect to the vaccinia promoter was identified and designated pSB2 (also known as pSCB2).

CV-1 cells were infected with vaccinia virus and transfected with pSB2 using the methods described in reference 17. The recombinant virus was TK⁻ due to the insertional inactivation of the vaccinia TK gene and this phenotype provided a means for easy isolation. TK⁻ viruses were selected from the resulting progeny by plating on 143-TK⁻ cells in the presence of 5-bromodeoxyuridine, and such virus clones were screened for the presence of HCMV specific DNA inserts by hybridisation with pSB1. After virus growth and purification the genome of the recombinant virus was analysed by restriction endonuclease digestion and Southern blotting. The results confirmed that the HCMV gB gene had been inserted into the vaccinia TK gene within the HindIII J fragment and showed that no other genomic rearrangements had occurred. The recombinant virus was termed HCMV gB-VAC.

Expression of HCMV gB by Recombinant Vaccinia Virus

To test for expression of HCMV gB, polyvalent rabbit serum raised against purified HCMV was used to immunoprecipitate $^{35}$S-labelled polypeptides from cells infected with HCMV gB-VAC or WT vaccinia.

CV-1 cells were infected at 30 plaque forming units (pfu)/cell with either WT vaccinia or recombinant HCMV gB-VAC. 3 hours post-infection the cells were washed in methionine-free free medium and then incubated in methionine-free medium for 30 mins. The cells were labelled with 100 $\mu$Ci/ml of $^{35}$S-methionine in medium containing 10 $\mu$M unlabelled methionine. After washing in PBS, the cells were lysed in RIPA buffer (0.05 M Tris HCl pH 7.2, 0.15 M NaCl, 1% sodium deoxycholate, 0.1% SDS, 1% Triton x-100, 5 $\mu$g/ml DNase, 2 mM PMSF) for 10 mins, on ice. The lysate was centrifuged at 31,000 rpm (Beckman SW50.1 rotor) for 60 mins at 4° C. and aliquots of the resultant supernatant incubated (20 mins, room temperature) with either non-immune rabbit serum or serum from a rabbit hyperimmunised with HCMV. Immune complexes were precipitated with protein A sepharose (2 hrs room temperature), eluted, boiled and electrophoresed on 10% polyacylamide gels. The gel was fixed in methanol/acetic acid and impregnated with fluorographic enhancer (Amplify, Amersham) and autoradiographs prepared. Protein molecular weight markers were from HSV-1 infected cells, immunoprecipitated with monoclonal antibodies against the major capsid antigen (157 kD), glycoprotein B (128 kD) and VP16 (66 kD).

Using immune serum a polypeptide of approximately 145 kD was immunoprecipitated from cells infected with HCMV gB-VAC but not WT vaccinia infected cells. Other polypeptides were nonspecifically precipitated as shown by their reactivity with preimmune rabbit sera.

Murine monoclonal antibodies raised against HCMV and shown to have neutralising activity in vitro were next tested for their ability to recognise the HCMV gB product in HCMV gB-VAC infected cells. Plaques formed by HCMV gB-VAC on CV-1 cell monolayers were fixed with methanol and then incubated with monoclonal antibody and subsequently with either $^{125}$I-labelled Staphylococcus protein A (Amersham) or peroxidase-conjugated rabbit anti-mouse immunoglobulin (Dako). The virus plaques containing antigen recognised by the monoclonal antibody were viualised as black dots on autoradiographs in the case of protein-A binding antibodies or as "red plaques" following addition of $H_2O_2$ and amino-ethyl carbazole to monolayers reacted with peroxidase-conjugated antiglobulin. Of ten monoclonal antibodies tested four were shown to recognise plaques formed by HCMV gB-VAC but not WT vaccinia. It was noteworthy that all the plaques formed by the HCMV gB-VAC bound the monoclonal antibody indicating the virus was a pure stock not contaminated with WT vaccinia. Similar conclusions were reached from plaquing with virus on TK⁻ 143 cells in the presence and absence of bromodeoxyuridine, and by the analyses of genomic DNA by Southern blotting.

Cell lysates from WT vaccinia, recombinant HCMV gB-VAC or uninfected CV-1 cells were prepared and immunoprecipitated with monoclonal antibodies 37, 39 or 59 as described above.

Three monoclonal antibodies that were able to bind Protein A also immunoprecipitated $^{35}$S-methionine-labelled infected cell extracts. Consistent with the immuno-staining data, the monoclonal antibodies 37 and 39 immunoprecipitated proteins from cells infected with HCMV gB-VAC but not WT vaccinia or uninfected cells. Monoclonal antibody 59 did not recognise HCMV gB although this antibody could neutralise HCMV infectivity. The target protein of this antibody is unknown. In addition to the 145 kD protein a smaller protein of approximately 55 kD was also detected with both monoclonal antibodies. This suggests that the epitope(s) recognised by both monoclonal antibodies are present on both the 55 kD and 145 kD proteins, or that these proteins are physically associated and consequently coprecipitate.

To make a direct comparison of the gB synthesised in HCMV-infected cells with gB from HCMV gB-VAC infected cells, MRC-5 cells were infected at 5 pfu/cell with HCMV strain AD169 or mock-infected. Cells were labelled with $^{35}$s-methionine (28 $\mu$Ci/ml) from 72–98 hrs post-infection and lysates prepared and immunoprecipitated with either monoclonal antibody 39 or 47 as described above. CV-1 cells infected with WT vaccinia, recombinant gB-VAC or uninfected were radiolabelled, lysed and immunoprecipitated with monoclonal antibody 39 as described above.

The 145 kD species synthesised in both systems clearly comigrated and the mature 55 kD species did also, although nonspecific precipitation of a similar sized vaccinia band made this less clear. In addition to these two species, an additional 66 kD band was also visible in HCMV infected cell lysates. This is thought to be unrelated to gB since another monoclonal antibody (47) that did not bind protein A brought down this band nonspecifically. Its size suggested it may be the abundant 66 kD HCMV matrix protein.

Human Immune Serum Recognises HCMV gB

To investigate whether antibodies directed against HCMV gB are produced during a primary HCMV infection in man, sera taken from a cardiac transplant patient before and after primary HCMV infection were tested for the ability to recognise HCMV gB synthesised by recombinant vaccinia virus.

CV-1 cells, infected with either H3-VAC or HCMV gB-VAC were labelled with $^{35}$S-methionine cell lysates prepared as described above. Lysates were then tested sequentially with either rabbit pre-immune followed by rabbit anti-HCMV, or human sera taken before HCMV infection followed by sera after HCMV infection. Immune complexes were precipitated with protein A sepharose and separated on polyacrylamide gels as described above.

Rabbit serum raised against HCMV was used as a positive control. Since it was likely that the human sera also contained antibodies to vaccinia virus, owing to previous smallpox vaccination, the immune precipitations were carried out sequentially using sera taken before and then after HCMV infection on the same cell lysate. These data show that 145 kD polypeptide was immunoprecipitated from gB-VAC-infected cell lysates by human sera taken after but not before HCMV infection. The 145 kD protein was also precipitated by the rabbit anti-HCMV sera. As a further control the same human sera were tested for ability to recognise the influenza virus haemagglutinin (HA) from influenza virus A/NT/60/68 expressed by another recombinant vaccinia virus H3-VAC. The influenza HA was immunoprecipitated by human sera taken before HCMV infection and to a lesser extent sera taken after HCMV infection. These data demonstrate that the cardiac transplant patient had experienced a previous influenza A virus infection of the H3 subtype. Moreover, the precipitation of influenza HA by sera taken prior to HCMV infection, while HCMV gB was only precipitated by sera taken after HCMV infection, confirm the specificity of the precipitation of the HCMV protein. It is also significant that the development of antibodies against HCMV occurred despite immunosuppression during cardiac transplantation to prevent tissue rejection. The human immune serum was also able to neutralise HCMV infectivity in vitro. Several other sera taken from cardiac transplant patients who experienced HCMV infections during immunosuppression also yielded similar precipitation of HCMV gB.

HCMV gB is Expressed on the Infected Cell Surface

To examine whether the HCMV gB synthesised in cells infected with recombinant vaccinia virus is transported to the cell surface immunofluorescence studies were performed.

CV-1 cells were grown on glass coverslips and infected with either WT vaccinia virus or HCMV-gB-VAC at 10 pfu/cell. 48 hrs post-infection cells were fixed with an isotonic solution of 2% paraformaldehyde. Following incubation in PBS containing 4% bovine serum albumin (BSA) monolayers were reacted with 1/400 dilution of monoclonal antibody 37 antibody containing ascitic fluid overnight at 4° C. After extensive washing bound antibody was detected with fluorescein conjugated rabbit anti-mouse immunoglobulin (Dako) diluted 1/20 in PBS containing 4% BSA and 2% normal rabbit serum. Fluorescence was observed with u.v. illumination at ×400.

The HCMV gB-VAC infected cells showed positive surface fluorescence while WT infected cells showed only background reactivity. The pattern of staining on the infected cell membrane was unusual showing a granular appearance, suggesting clustering or aggregation of HCMV gB in the cell membrane.

Vaccination of Rabbits with HCMV gB-VAC

To determine if anti-serum raised against HCMV gB expressed by recombinant vaccinia virus could neutralise HCMV infectivity, two rabbits were vaccinated with the live recombinant virus, as indicated in Table 1.

TABLE 1

| Neutralisation of HCMV by rabbit sera | | | | |
|---|---|---|---|---|
| Day post vaccination | HCMV plague reduction (%) | | | |
| | Rabbit 1 | | Rabbit 2 | |
| | 1/10 | 1/50 | 1/10 | 1/50 |
| 0 | 0 | 0 | 0 | 0 |
| 46 | 54 | 30 | 40 | 16 |
| 59 | 69 | 60 | 57 | 76 |
| 76 | 70 | 61 | 48 | 30 |
| 116 | 67 | 68 | 55 | 25 |
| 151 | 97 | 87 | 77 | 77 |

The two rabbits were vaccinated intradermally with $10^8$ pfu of purified infectious HCMV gB-VAC into one site on each flank. On day 46 both animals were revaccinated with the same dose of live recombinant virus. A third rabbit received a TK⁻ recombinant vaccinia virus expressing the influenza virus nucleoprotein gene and was also revaccinated. Serum samples obtained from rabbits on the days indicated in Table 1 were tested for their ability to neutralise HCMV infectivity in vitro. Serum samples were incubated at 56° C. for 30 mins to inactivate complement and then one volume of serum dilution (1:10 or 1:50) was mixed with an equal volume of HCMV strain AD169 (750 pfu) and incubated at 37° C. for 30 mins. Fresh rabbit serum was added to a final concentration of 5% as a source of complement and the mixture incubated for a further 30 mins at 30° C. before the residual virus was assayed on MRC-5 cells. Plaques were counted 10 days later and the results in Table 1 are expressed as a percentage reduction in plague numbers. Serum from both rabbits 1 and 2 contained antibodies that neutralised HCMV infectivity in the presence of exogenous complement. A third rabbit inoculated with a different TK⁻ recombinant vaccinia virus did not posses such antibodies.

The two animals vaccinated with HCMV gB-VAC thus developed antibodies that neutralised HCMV in vitro while the third rabbit that was immunised with another TK⁻ recombinant vaccinia virus expressing the influenza virus nucleoprotein did not. The neutralisation of HCMV infectivity by these rabbit sera was dependent upon complement since heat inactivated sera failed to reduce HCMV plaque numbers without addition of exogenous complement. Additional experiments examining the level of antibodies before and before secondary vaccination indicated that both animals had increased antibody titres following revaccination. Rabbit 1 maintained its antibody level up to day 116 and at this time reduced HCMV plaque formation by 70% at a 1:50 dilution. The level of antibodies in rabbit 2 decreased with time, but still reduced HCMV plaque formation by 24% at a 1:50 dilution on day 116.

CONCLUSIONS

The putative coding sequence codes for an authentic HCMV protein that has been expressed in vaccinia. The protein expressed in vaccinia is electrophoretically identical to a protein seen in HCMV infected cells. The protein has the following properties. It is a target for neutralising antibody (because it is recognised by a neutralising antibody). It is present on the surface of cells infected with HCMV gB-VAC, and it is present in the HCMV particle.

The primary product has an apparent molecular weight of 145,000 and is processed to a product of molecular weight 55,000. It is able to induce production of antibodies that neutralise HCMV infectivity when delivered to the rabbit immune system via expression in recombinant virus infected cells.

Although the above example used HCMV strain AD169, it will be appreciated that other strains are functionally equivalent and could also be used.

The HCMV Glycoportein H

A comparison of the deduced amino acid sequence of this gene as shown in FIG. 5 with that of EBV and HSV-1 genes showed homology with glycoprotein H of these viruses. Consequently this HCMV gene is subsequently referred to as HCMV gH.

Construction of Recombinant Vaccinia Virus Expressing HCMV of gH

The HCMV gH gene was cloned into plasmid vectors pGS62 as follows. The 11400 base pair HindIII L fragment was excised from plasmid pAT153/HindIII L by digestion with HindIII and the termini made blunt-ended by treatment with E. coli DNA polymerase Klenow fragment. The DNA was then digested with SmaI which cuts 96 nucleotides upstream of the translational initiation site of the CMV gH gene, as shown in FIG. 5. A 2.5 kb DNA fragment containing the HCMV gH coding sequence was isolated and ligated into plasmid pGS62 at the unique SmaI site. A resultant plasmid pSB3 was shown to contain the HCMV gH gene correctly positioned downstream of a vaccinia promoter. The foregoing procedure was essentially similar to that used for the HCMV gB gene.

The HCMV gH was also inserted into plasmid pSC11 (reference 16) at the unique SmaI site downstream of the same vaccinia promoter. This plasmid was called pSB4. Plasmid SC11 contains a second vaccinia promoter driving expression of β-galactosidase gene. Consequently, recombinant viruses which pick up the HCMV gH gene simultaneously also acquire the β-galactosidase gene. This permits rapid identification of plaques formed by these recombinant viruses by virtue of their blue colour in the presence of X-gal.

Plasmid pSB3 and pSB4 were used to construct TK⁻ recombinant vaccinia viruses containing the HCMV gH gene. The viruses were called HCMV gH-VAC (GS62) and HCMV gH-VAC (SC11), respectively. These viruses were plaque purified and then larger stocks grown and purified using established methods (reference 17). Analyses of the genomic DNA of viruses showed that as predicted the HCMV gH gene was inserted into the TK gene with the vaccinia HindIII J fragment.

Expression of the HCMV gH Gene

The product of the HCMV gH gene was identified by HCMV gH-VAC infected cells as follows:

(1) Monolayers of CV-1 cells were infected with either WT vaccinia (WT) or recombinant vaccinia viruses CMB gH-VAC (GS62) or CMV gH-VAC (SC11). Infected cells were radio-labelled with $^{35}$S-methionine from 3 to 6 hours post infection and lysates prepared from the infected cells 6 hours post infection. These lysates were immunoprecipitated with either a nonspecific rabbit sera, rabbit sera raised against purified HCMV virions or anti-HCMV monoclonal antibody 16 (HCMV 16). A polypeptide of approximately 86 kD was immunoprecipitated from gH-VAC (SC11) and gH-VAC (GS62) infected cells using rabbit anti-HCMV serum. This polypeptide was not precipitated from WT vaccinia infected cells. A rabbit serum raised against a synthetic peptide from HSV glycoprotein D failed to precipitate this band. However, a polypeptide of similar size was precipitated from HCMV infected MRC-5 cells using the rabbit anti-HCMV serum.

(2) Anti-HCMV monoclonal 16 also immunoprecipitated a band of 86 kD from gH-VAC but not WT infected cells. As a control, monoclonal HCMV 37 which recognises HCMV gB did not precipitate the 86 kD protein.

(3) The cellular location of HCMV gH synthesised in HCMV gH-VAC infected cells was investigated by immunofluorescence. This showed that the gH polypeptide was transported to the nuclear membrane, and was also detectable in the cytoplasma diffusely. There was no fluorescence on HCMV gH-VAC infected cells unless the cells were first permeabilised. Monoclonal HCMV 16 neutralises HCMV Infectivity To investigate if HCMV gH is a target for antibody mediated neutralisation of virus infectivity, HCMV was incubated with monoclonal HCMV 16 and residual infectivity assayed on MRC-5 cells. Even at a dilution of 1:4000 monoclonal HCMV 16 reduced HCMV infectivity in vitro by greater than 50%. This neutralisation was not dependent upon exogenous complement. Clearly the product of the HCMV gH gene is a target for virus neutralisation and hence has potential in future HCMV vaccines.

CONCLUSIONS

The DNA sequence of a HCMV glycoprotein gene that maps within the HindIII L fragment of HCMV was determined and expressed in recombinant vaccinia virus. The gene product was identified as an 86 kD polypeptide that is transported to the nuclear membrane in recombinant vaccinia infected cells. In HCMV infected cells it is also in the cell surface membrane. A monoclonal antibody which recognises this protein efficiently neutralises the infectivity of HCMV in vitro. This demonstrates the potential role of this 86 kD glycoprotein in HCMV vaccines.

While the foregoing description has concentrated, by way of example, on the production of the HCMV proteins in cells infected with recombinant vaccinia virus, and the potential of said virus to act as a vaccine in causing the host to raise protective antibodies; it will be apparent that the present invention is exploitable in a variety of different ways using technology readily within the capability of those of ordinary skill in the art. These are exemplified as follows.

(i) On the basis of the DNA and amino acids sequences given in FIGS. 3 and 6, DNA encoding HCMV gB and gH proteins can be obtained by methods well known to those skilled in the art. For example, DNA encoding the desired amino acid sequence can be synthesised. Alternatively, the DNA can be obtained from the viral genome by restriction followed by hybridisation with labelled oligonucleotide probes to identify the sequence of interest. Also, cDNA could be obtained by reverse transcription from viral mRNA, followed by screening with oligonucleotide hybridisation probes.

(ii) The HCMV proteins can be expressed in microorganisms or cell cultures transformed with recombinant DNA vectors. Suitable vectors and expression systems are widely known and used for expressing protein in for example bacteria such as Escherichia coli, yeasts such as Saccharomyces cerevisiae, and mammalian cell cultures such as COS or CHO cells. In the case of microbial expression (e.g. bacteria and yeasts), the HCMV protein DNA will normally be manipulated so as to delete the 5' flanking region before insertion into the expression vector, the coding region being translated from a start codon which is either the ATG of HCMV protein gene or one which is artificially introduced in reading frame with the coding sequence. The latter possibility will be used particularly if it is desired to delete a 5' region of the coding sequence, such as the hydrophobic signal region. The hydrophobic 3' anchor region may also be omitted, if desired, since it is unlikely that it contains a critical antigenic determinant. The recombinant vector may contain more than one HCMV protein coding sequence, e.g. tandem repeats of a coding sequence of gB or gH, or coding sequences of both gB and gH in tandem. In order to reduce the size of the expression vector, a part only of each glycoprotein coding sequence may be incorporated, so long as it correctly encodes the desired antigenic determinant.

(iii) The HCMV proteins, or portions thereof containing the desired antigenic determinant, can also be synthesised by chemical means, using known methods of protein synthesis.

(iv) The HCMV protein, however produced, can be used to produce HCMV-specified antibody, for example as a monospecific serum by immunising a suitable animal with the HCMV protein, allowing the animal to raise antibodies to the protein, and then extracting the antiserum from the animal.

(v) The HCMV protein can be used in particular to produce HCMV-specific monoclonal antibodies, by the standard technique of immunisation of an animal, usually a mouse, with the protein, followed by fusion of spleen cells from the animal with tumour cells to form antibody-producing hydridomas which can be separated and cloned. From these clones can be harvested the monoclonal antibodies. Normally a panel of antibodies will be produced, since each HCMV protein will be expected to raise more than one antibody.

(vi) The HCMV protein can also be used to purify HCMV-specific antibodies, e.g. by contacting the antibodies with the protein immobilised on a suitable support, such as an affinity column; and then separating the bound antibodies from the protein such as by elution.

(vii) The HCMV protein can also be used in assays for HCMV antibody. A variety of conventional assay procedures can be used, based for example on ELISA, RIA or immunofluorescence. Typically, the HCMV protein could be immobilised on a support, then contacted with the clinical sample from a human subject. After washing, the support is contacted with labelled anti-human IgG which binds to any HCMV antibody which has been found by the immobilised HCMV protein.

(viii) The HCMV protein can also be used as a vaccine, by compounding it with a suitable adjuvant or excipient of the kind conventionally employed in vaccine formulations. This form of vaccine might be more appropriate than the recombinant vaccine for example in immunosuppressed individuals.

REFERENCES

1. Stinski, M. (1976) J. Virol. 19, 594–609.
2. Pereira, L., Hoffman, M., Tatsuno, M and Dondero, D. (1984) Virology, 139, 73–86.
3. Pereira, L., Hoffman, M. and Cremer, N. (1982) Infect. Immun., 36, 933–942.
4. Pereira, L., Hoffman, M., Gallo, G. and Cremer, N. (1982) Infect. Immun., 36, 924–932.
5. Britt, W. J. (1984) Virology, 135, 369–378.
6. Nowak, B., Sullivan, C., Sarnow, P., Thomas, R., Bricout, F., Nicolas, J. C., Fleckenstein, B. and Levine, A. J. (1984) Virology, 132, 325–338.
7. Law, K. M., Wilton-Smith, P. and Farrar, G. H. (1985) J. Med. Virol. 17, 255–266.
8. Rasmussen, L., Mullenax, J., Nelson, R. and Merigan, T. C. (1985) J. Virol. 55, 274–280.
9. Rasmussen, L., Mullenax, J., Nelson, M. and Merigan, T. C. (1985) Virology, 145, 186–190.
10. Britt, W. J. and Auger, D. (1986) J. Virol., 58, 185–191.
11. Sanger, F., Coulson, A. R., Barrell, B. G., Smith, A. J. H. and Roe, B. A. (1980) J. Mol. Biol., 143, 161–178.
12. Bankier, A. T. and Barrell, B. G. (1983). Shotgun DNA sequencing in Techniques in the Life Sciences. Volume B508, pp. 1–34. Elsevier Scientific Publishers Ireland Ltd.

13. Oram, J. D., Downing, R. G., Akrigg, A., Dollery, A. A., Duggleby, C. J., Wilkinson, G. W. G. and Greenaway, P. J. (1982) J. Gen. Virol., 59, 111–129.
14. Pellet, P. E., Biggin, M. D., Barrell, B. G. and Roizman, B. (1985) J. Virol. 56, 807–813.
15. Smith, G. L. and Moss, B. BioTechniques 2, 120–126, (1984).
16. Chakrabarti, S., Breckling, K. and Moss, B. (1985) Mol. Cell. Biol. 5, 3403–3409.
17. Mackett, M., Smith, G. L. and Moss, B. (1984) J. Virol. 47, 857–864.
18. Boyle, D. B., Couper, B. E. H. and Both, G. W. (1985) Gene, 35, 169–177.
19. Twigg, A. J. and Sherratt, D. (1980) Nature, 283, 216.

What is claimed is:

1. Human cytomegalovirus (HCMV) monospecific polyclonal antisera prepared by a method comprising the following steps:
   (a) expressing from a recombinant DNA vector in a suitable host organism an HCMV glycoprotein polypeptide capable of raising HCMV antibodies in humans, wherein said polypeptide is selected from the group consisting of (i) an HCMV glycoprotein B (gB) polypeptide comprising an amino acid sequence as depicted in FIG. 3; (ii) an HCMV gB polypeptide from an HCMV strain functional equivalent to HCVM strain AD 169; and (iii) the HCMV gB of (i) or (ii) lacking the C-terminal membrane anchor sequence;
   (b) immunizing a host animal with the polypeptide of step (a); and
   (c) isolating monospecific antiserum from the host animal that is specific to said polypeptide.

2. Human cytomegalovirus (HCMV) monospecific polyclonal antisera prepared by a method comprising the following steps:
   (a) providing a recombinant virus vector containing DNA encoding an HCMV glycoprotein polypeptide capable of raising HCMV antibodies in humans, wherein said polypeptide is selected from the group consisting of (i) an HCMV glycoprotein B (gB) polypeptide comprising an amino acid sequence as depicted in FIG. 3; (ii) an HCMV gB polypeptide from an HCMV strain functionally equivalent to HCVM strain AD 169; and (iii) the HCMV gB of (i) or (ii) lacking the C-terminal membrane anchor sequence;
   (b) immunizing a host animal with the recombinant virus vector of step (a); and
   (c) isolating monospecific antiserum from the host animal that is specific to said polypeptide.

3. HCMV monospecific polyclonal antisera according to claim 2, wherein said polypeptide is selected from the group consisting of (i) an HCMV glycoprotein B (gB) polypeptide comprising an amino acid sequence as depicted in FIG. 3; and (ii) the HCMV gB of (i) lacking the C-terminal membrane anchor sequence.

4. Human cytomegalovirus (HCMV) monospecific polyclonal antisera prepared by a method comprising the following steps:
   (a) synthesizing an HCMV glycoprotein polypeptide capable of raising HCMV antibodies in humans, wherein said polypeptide is selected from the group consisting of (i) an HCMV glycoprotein B (gB) polypeptide comprising an amino acid sequence as depicted in FIG. 3; (ii) an HCMV gB polypeptide from an HCMV strain functionally equivalent to HCVM strain AD 169; and (iii) the HCMV gB of (i) or (ii) lacking the C-terminal membrane anchor sequence;
   (b) immunizing a host animal with the polypeptide of step (a); and
   (c) isolating monospecific antiserum from the host animal that is specific to said polypeptide.

5. HCMV monospecific polyclonal antisera according to claim 4, wherein said polypeptide is selected from the group consisting of (i) an HCMV glycoprotein B (gB) polypeptide comprising an amino acid sequence as depicted in FIG. 3, or (ii) an HCMV gB polypeptide from an HCMV strain functionally equivalent to HCVM strain AD 169.

6. HCMV monospecific polyclonal antisera according to claim 4, wherein said polypeptide is selected from the group consisting of (i) an HCMV glycoprotein B (gB) polypeptide comprising an amino acid sequence as depicted in FIG. 3; and (ii) the HCMV gB of (i) lacking the C-terminal membrane anchor sequence.

7. HCMV monospecific polyclonal antisera according to claim 5, wherein said polypeptide is selected from the group consisting of (i) an HCMV glycoprotein B (gB) polypeptide comprising an amino acid sequence as depicted in FIG. 3; and (ii) the HCMV gB of (i) lacking the C-terminal membrane anchor sequence.

* * * * *